United States Patent
Nguyen

(10) Patent No.: US 10,206,706 B2
(45) Date of Patent: Feb. 19, 2019

(54) INNER TUBULAR MEMBER FOR ANGLED ROTARY SURGICAL INSTRUMENT

(71) Applicant: MEDTRONIC-XOMED, INC., Jacksonville, FL (US)

(72) Inventor: Thoai Nguyen, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 323 days.

(21) Appl. No.: 14/725,824

(22) Filed: May 29, 2015

(65) Prior Publication Data

US 2016/0345997 A1     Dec. 1, 2016

(51) Int. Cl.
| A61B 17/3205 | (2006.01) |
| A61B 17/32 | (2006.01) |
| A61B 17/3207 | (2006.01) |
| A61B 17/29 | (2006.01) |

(52) U.S. Cl.
CPC .... *A61B 17/3205* (2013.01); *A61B 17/32002* (2013.01); *A61B 17/320783* (2013.01); *A61B 2017/2905* (2013.01); *A61B 2017/320032* (2013.01)

(58) Field of Classification Search
CPC .......... A61B 17/32002; A61B 17/3205; A61B 17/320783; A61B 17/2905; A61B 17/320032

See application file for complete search history.

(56) References Cited

U.S. PATENT DOCUMENTS

| 4,811,736 A | 3/1989 | Griggs et al. |
| 5,411,514 A | 5/1995 | Fucci et al. |
| 5,540,708 A | 7/1996 | Lim et al. |
| 5,620,447 A | 4/1997 | Smith et al. |
| 5,707,350 A | 1/1998 | Krause et al. |
| 5,833,692 A * | 11/1998 | Cesarini .......... A61B 17/32002 606/170 |
| 5,922,003 A | 7/1999 | Anctil et al. |
| 5,972,000 A | 10/1999 | Beyar et al. |
| 6,193,686 B1 | 2/2001 | Estrada et al. |
| 6,312,438 B1 | 11/2001 | Adams |
| RE38,018 E | 3/2003 | Anctil et al. |

(Continued)

FOREIGN PATENT DOCUMENTS

| EP | 0 592 249 | 4/1994 |
| GB | 2 433 700 | 7/2007 |

(Continued)

OTHER PUBLICATIONS

PCT International Search Report and Written Opinion dated Jul. 22, 2016, 14 pages.

*Primary Examiner* — Julie A Szpira
(74) *Attorney, Agent, or Firm* — Dicke, Billig & Czaja, PLLC

(57) ABSTRACT

An inner member rotatable in an angled outer tubular member of a rotary surgical cutting instrument includes first and second tubular members. The first tubular member includes rigid proximal and distal portions comprised of a first material and a flexible intermediate portion comprised of a second material. The proximal portion includes a hub. The distal portion terminates at a distal end configured to couple with a cutting tip. The intermediate portion extends between and is fixedly coupled to the proximal and distal portions.

17 Claims, 4 Drawing Sheets

(56) References Cited

U.S. PATENT DOCUMENTS

| | | | |
|---|---|---|---|
| 6,533,749 B1* | 3/2003 | Mitusina | A61B 17/32002 604/22 |
| 6,656,195 B2 | 12/2003 | Peters et al. | |
| 7,338,495 B2 | 3/2008 | Adams | |
| 8,052,706 B2 | 11/2011 | Mitusina | |
| 8,057,500 B2 | 11/2011 | Mitusina | |
| 8,202,288 B2 | 6/2012 | Adams et al. | |
| 8,623,266 B2 | 1/2014 | Adams | |
| 8,828,036 B2 | 9/2014 | Flynn et al. | |
| 8,940,005 B2 | 1/2015 | Edwards | |
| 9,247,952 B2* | 2/2016 | Bleich | A61B 17/1671 |
| 2005/0277970 A1 | 12/2005 | Norman et al. | |
| 2007/0016099 A1* | 1/2007 | Chin | A61B 10/0275 600/565 |
| 2009/0192495 A1 | 7/2009 | Ostrovsky et al. | |
| 2010/0087711 A1* | 4/2010 | Edwards | A61B 17/32002 600/139 |
| 2011/0160731 A1* | 6/2011 | Bleich | A61B 17/29 606/79 |
| 2013/0053830 A1* | 2/2013 | Edwards | A61B 17/32002 606/1 |
| 2013/0110145 A1* | 5/2013 | Weitzman | A61B 17/1642 606/170 |
| 2015/0282833 A1* | 10/2015 | Yoon | A61B 17/32002 606/114 |
| 2016/0143656 A1* | 5/2016 | Tasci | A61B 17/3205 606/170 |

FOREIGN PATENT DOCUMENTS

| | | |
|---|---|---|
| WO | 1996/25103 | 8/1996 |
| WO | 1998/17187 | 4/1998 |
| WO | 2001/22889 | 4/2001 |
| WO | 2012/060959 | 5/2012 |

* cited by examiner

INNER TUBULAR MEMBER FOR ANGLED ROTARY SURGICAL INSTRUMENT

BACKGROUND

Angled rotary tissue cutting instruments have become widely accepted for use in various surgical procedures to cut anatomical tissue at a surgical site within a patient's body. Angled rotary tissue cutting instruments typically comprise an elongate angled outer member and an elongate flexible inner member rotatably disposed within the angled outer member. A cutting element at a distal end of the inner member is exposed from an opening at a distal end of the outer member to cut anatomical tissue at the surgical site when the inner member is rotated within the outer member. The inner member is ordinarily rotated within the outer member via a powered surgical handpiece coupled to proximal ends of the outer and inner members, with the handpiece being maintained external of the patient's body. The outer member has one or more angled, curved or bent regions along its length to provide an angled configuration that facilitate positioning of the cutting element at the surgical site when the instrument is introduced in the patient's body, and particularly when the instrument is introduced through a narrow or small size, natural or artificially created entry opening in the patient's body. The inner member is provided with one or more flexible regions to reside within the one or more angled, curved or bent regions of the outer member for transmitting torque to rotate the cutting element while conforming to the angled configuration of the outer member. The angled configuration of the outer member is particularly beneficial in facilitating positioning of the cutting element at the surgical site where there is a non-linear path in the body form the entry opening to the surgical site. In such cases, angled rotary tissue cutting instruments are usually better suited to access the surgical site more easily and quickly, and with less trauma to the patient, than are rotary tissue cutting instruments in which the outer member is longitudinally straight.

In many surgical procedures performed using rotary tissue cutting instruments, the internal lumen of the inner member is used to transmit suction to the surgical site to aspirate anatomical tissue and/or fluid through the inner member. In addition, an annular gap or clearance between the internal diameter of the outer member and the external diameter of the inner member is commonly used as an irrigation passage to supply irrigation fluid to the surgical site. While rotary tissue cutting instruments with curved or bendable shafts have been used for some time, these shafts typically employ a single spirally wound strip of material to impart flexibility while transmitting torque. Unfortunately, spirally wound shafts and couplings tend to unwind when rotated in a direction opposite their winding so that torque can only be transmitted efficiently in one direction. A loss of irrigation can occur due to the inner member including spiral cuts or coils along the flexible region formed gaps as the inner member rotatably conforms to the angled configuration of the outer member while rotating. The loss of irrigation can be critical in many applications. For example, in a neuro tumor resection device, Micro-Electro-Mechanical (MEM) component are often used in which the loss of irrigation can cause the device to clog, leading to failure. In other devices, such as in an Ear-Nose-Throat (ENT) micro-debrider, the device can become less effective with the loss of irrigation due to not having enough saline at the cutting tip.

Angled rotary tissue cutting instruments continue to be extremely useful. There is a need for an elongated tubular assembly capable of maintaining sufficient strength and rigidity when transmitting torque via the flexible regions, and prevent a loss of irrigation, particularly considering that angled rotary tissue cutting instruments must oftentimes be designed to operate at high rotational speed and to withstand the forces imposed when cutting hard or tenacious anatomical tissue.

SUMMARY

One aspect of the present disclosure relates to an inner member rotatable within an angled outer tubular member of a rotary surgical cutting instrument. The inner member includes a first tubular member. The first tubular member includes a rigid proximal portion comprised of a first material. The proximal portion includes a hub. A flexible intermediate portion is comprised of a second material. A rigid distal portion is comprised of the first material. The distal portion terminates at a distal end configured to couple with a cutting tip. The flexible intermediate portion extends between and is fixedly coupled to the proximal portion and the distal portion.

Another aspect of the present disclosure relates to an inner member rotatable within an angled outer tubular member of a rotary surgical instrument, the inner member includes a first tubular member. The first tubular member has a proximal portion, a distal portion, and an intermediate portion extending between the proximal portion and the distal portion. The proximal and distal portions are comprised of a rigid material. The intermediate portion is comprised of a flexible thermoplastic material.

Another aspect of the present disclosure relates to an angled rotary tissue cutting instrument including a rigid outer tubular member, an inner tubular member, and a handpiece. The rigid outer tubular member has a cutting window formed at a distal end, an opposing proximal end, and an angled region between the distal and proximal ends. The inner tubular member is coaxially disposed within the outer tubular member. The inner tubular member includes a first tubular member. The first tubular member has a proximal portion, a distal portion terminating at a cutting tip, and an intermediate portion extending between the proximal portion and the distal portion. The intermediate portion is comprised of a flexible material and the proximal and distal portions are comprised of a rigid material. The handpiece is configured to rotate the inner member within the outer member to selectively expose the cutting tip at the cutting window. The flexible region of the inner tubular member conforms to the angled region while being rotated within the outer tubular member.

DETAILED DESCRIPTION

Figure 1:
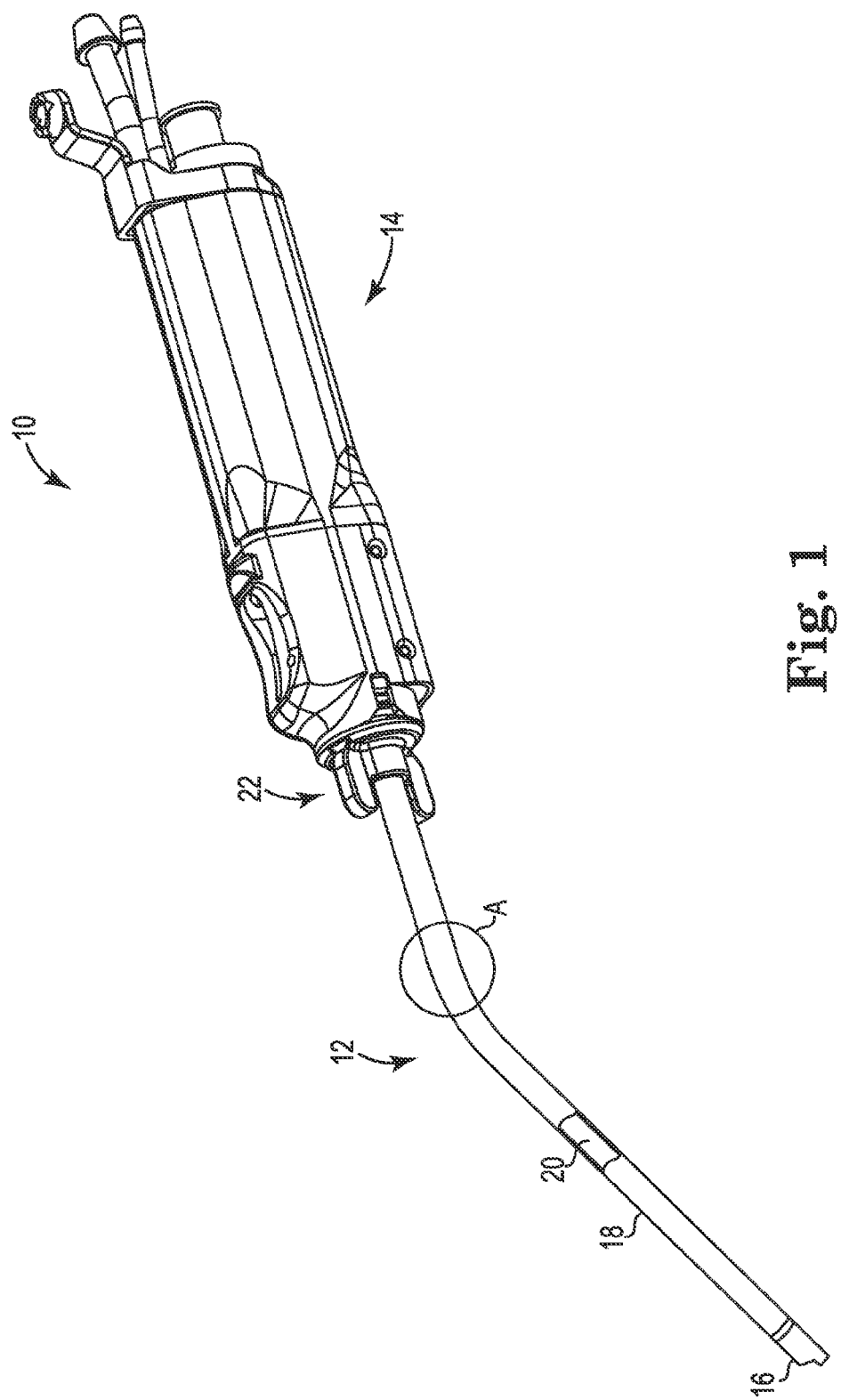
FIG. 1 is a perspective view of an angled rotary surgical cutting instrument in accordance with principles of the present disclosure.

One embodiment of a surgical cutting instrument in accordance with principles of the present disclosure 10 is illustrated in FIG. 1. The surgical cutting instrument 10 includes a cutting blade assembly 12 and a handpiece 14 (referenced generally in FIG. 1). In general terms, the cutting blade assembly 12 has a proximal end connected to the handpiece 14 and a distal end terminating at a cutter 16. The cutting blade assembly 12 includes an elongated outer member 18 and an elongated inner member 20 extending between the proximal and distal ends. The inner member 20 is coaxially disposed within the outer member 18. Optionally, the cutting blade assembly 12 can include a middle tubular member (not shown) coaxially disposed between the outer member 18 and inner member 20.

The inner member 20 is co-axially disposed within the outer member 18 such that a cutting tip is exposed at a cutting window of the cutter 16. The cutting window and cutting tip (not shown) combine to form the cutter 16 and can be any cutting window and cutting tip suitable to perform the desired procedure. A hub assembly 22 couples the outer and inner members 18, 20, respectively, to the handpiece 14 such that the tubular members 18, 20 are rotatable relative to one another and the handpiece 14. The cutting blade assembly 12 can have one or more curved, angled, or bent regions along its length. The terms curved, angled or bent can be used interchangeably herein. The location and degree of the curvature or bend is predetermined to suitably accommodate the desired surgical procedure. More particularly, the outer member 18 rigidly defines the appropriate angle(s) between the proximal and distal ends.

With continued reference to FIG. 1, the outer member 18 is an elongated tubular body defining a distal end, a proximal end, and a central lumen extending between the proximal end and the distal end. The central lumen generally defines a uniform diameter and is generally uniformly smooth. The inner member 20 is maintained within the central lumen of the outer member 18 such that an outer surface of the inner member 20 and an inner surface of the outer member 18 define an irrigation pathway to the cutter 16 when assembled. The central lumen of the outer member 18 is sized to accommodate the inner member 20 coaxially within and maintain the irrigation pathway between walls of the inner member 20 and outer member 18.

In general terms, the handpiece 14 includes a housing that contains a motor (not shown) for driving the rotational movement of the inner member 20. The handpiece 14 receives proximal ends of the inner and outer members 20, 18 for fluidly connecting internal irrigation and aspiration paths (each not shown) with fluid pathways, respectively, assembled to the handpiece 14. Regardless, the irrigation path formed within the handpiece 14 extends through the outer member 18 to the cutting window. Similarly, the aspiration pathway formed within the handpiece 14 fluidly extends through the inner member 20 to the cutting tip and is in fluid communication with a negative pressure source for applying a negative pressure, or vacuum, to the aspiration path, and thus to the inner member 20.

Figure 2:
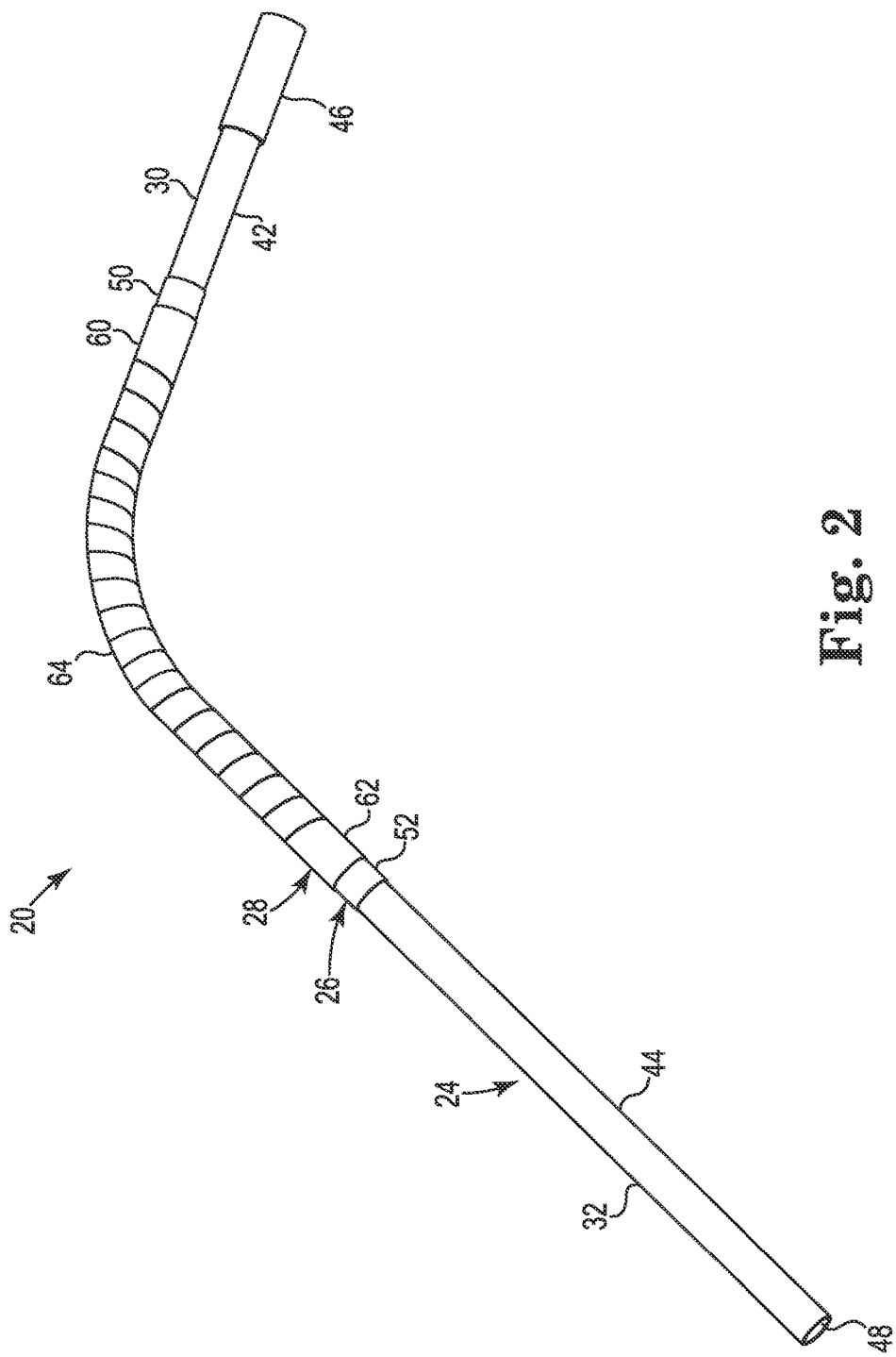
FIG. 2 is a perspective view of an inner member of the surgical cutting instrument of FIG. 1 in accordance with principles of the present disclosure.

With the above general construction of the surgical instrument 10 in mind, aspects of the inner member 20 of the cutting blade assembly 12 are shown in greater detail in FIG. 2. The inner member 20 defines a lumen between an open proximal end and a distal end. The inner member 20 includes a first tubular member 24 and a second tubular member 26 coaxially disposed around the first tubular member 24. In some embodiments, as discussed in greater detail below, the inner member 20 includes a third tubular member 28 coaxially disposed around the first and second tubular members 24, 26.

Figure 3:
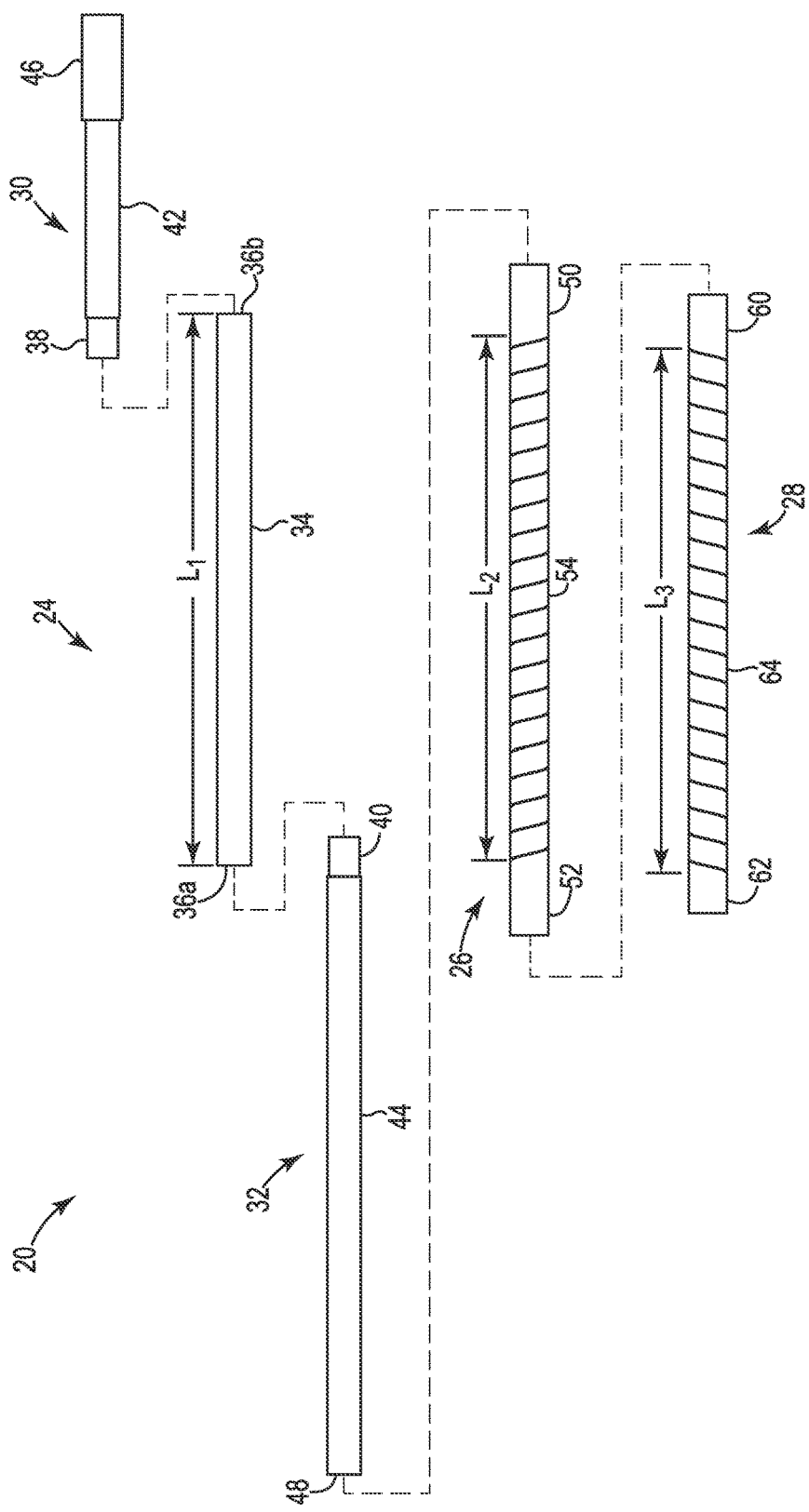
FIG. 3 is an exploded view of the inner member assembly of FIG. 2 in an unbent configuration in accordance with principles of the present disclosure.

Aspects of the inner member 20 are illustrated in the exploded view of FIG. 3. The first tubular member 24 includes a proximal portion 30, a distal portion 32, and an intermediate portion 34 extending between the proximal portion 30 and the distal portion 32. The proximal portion 30 and the distal portion 32 are formed of a rigid material such as stainless steel, for example. The intermediate portion 34 is formed of a flexible thermoplastic material such as Pebax®, for example. The intermediate portion 34 has a resistance to indentation deformation. The interior and exterior surfaces of intermediate portion 34 are generally smooth and are uninterrupted by grooves, cuts, etc. The first tubular member 24 maintains a fluid barrier along the tubular surfaces, preventing a loss of irrigation between the inner and outer members 18, 20.

Figure 4:
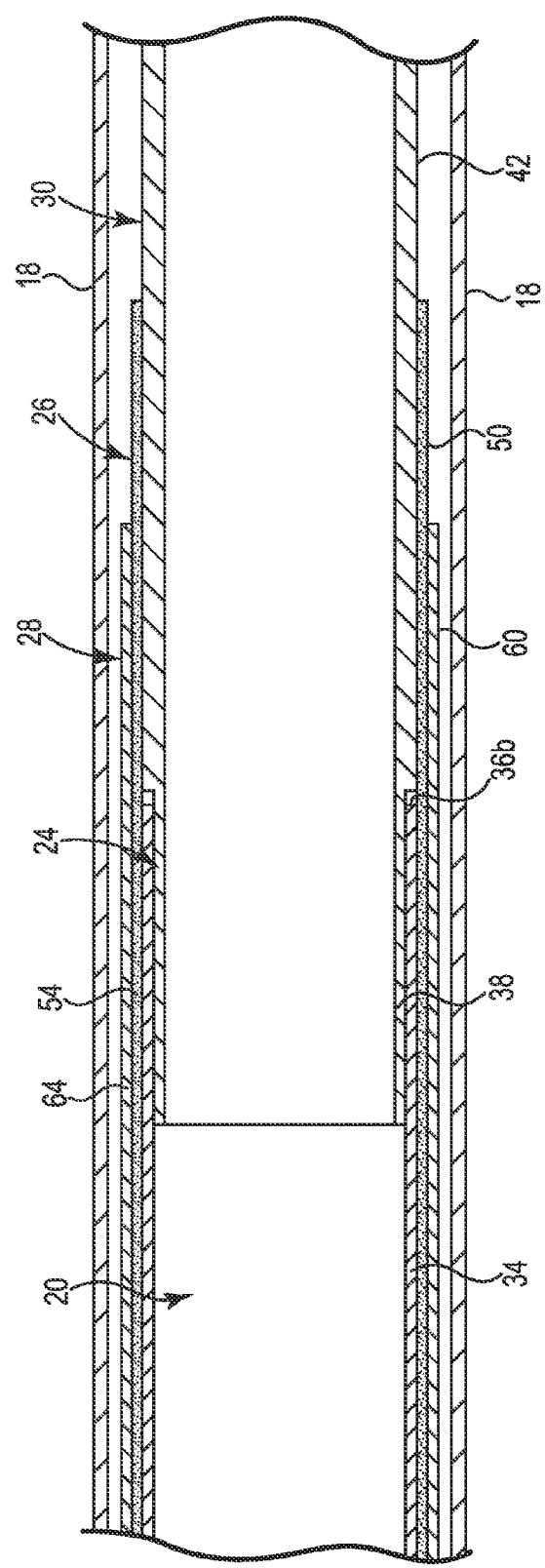
FIG. 4 is an enlarged partial cross-section view of a blade assembly of the surgical cutting instrument at Area A of FIG. 1 in accordance with principles of the present disclosure.

With additional reference to the partial exploded sectional view of FIG. 4, opposing first and second ends 36a, 36b of the intermediate portion 34 are coupled to the proximal and distal portions 30, 32, respectively. The proximal and distal portions 30, 32 can be fixedly secured to the intermediate portion 34 with an adhesive such as Loctite®, for example, by induction bonding, or by other means of bonding. The proximal and distal portions 30, 32 can include joining ends 38, 40 for coupling with the intermediate portion 34. The joining ends 38, 40 can have an outer diameter that is smaller, or inset from, an outer diameter of a main body 42, 44 of the proximal and distal portions 30, 32, respectively. The outer diameter of the joining ends 38, 40 closely corresponds with the inner diameter of the intermediate portion 34 such that the joining ends 38, 40 slidably mate within the intermediate portion 34. The joining ends 38, 40 provide a surface for coupling and bonding with the intermediate portion 34. The proximal portion 30 includes a hub 46 at a proximal end for connection with a handpiece of a surgical instrument (not shown). A distal end 48 of the distal portion 32 is suitable to connect with the cutting tip (not shown) of suitable nature to perform the desired procedure. An outer diameter of the intermediate portion 34 is substantially equivalent to the outer diameter of the distal and proximal portions 30, 32 along the main bodies 42, 44. The outer diameters of the main bodies 42, 44 are substantially equivalent. When assembled, the outer diameter of the first tubular member 24 is substantially consistent along the proximal, distal, and intermediate portions 30, 32, 34, with only the hub 46 having a larger diameter.

Although shown as linear in FIG. 3, the intermediate portion 34 is flexible and configured to conform to the curved or angled region(s) of the outer member 18 when the inner member 20 is coaxially disposed within the outer member 18. The inner member 20 is coaxially disposed within the outer member 18 such that the intermediate portion 34 of the inner member 20 is positioned along the bent or curved portion of the outer member 18. The intermediate portion 34 can be bent at any desired angle. For example, the intermediate portion 34 can be bent 20°, 45°, 90°, 120°, or even greater than 120°. Other angles suitable to provide for the desired application and procedure are also suitable. The intermediate portion 34 has a thickness sufficient to prevent kinking or breakage when rotated within the curved outer member 18.

With continued reference to FIGS. 2 through 4, the second tubular member 26 includes opposing proximal and distal sections 50, 52 and a central section 54 extending between the proximal and distal sections 50, 52. Although illustrated as linear in FIG. 3, the central section 54 includes a spiral cut pattern to provide longitudinal flexibility along the central section 54. The spiral cuts extend through a thickness of the second tubular member 26 between an outer surface and an inner surface. The spiral cut defines an angle with the central longitudinal axis of the second tubular member 26. The spiral cut defines a flexible region along the length of the second tubular member 26. The central section 54 provides flexibility and torque transmittance along the flexible region of the inner member 20 as the inner member 20 is rotated within, and conforms to, the shape of the bent or angled outer member 18.

When assembled with the first tubular member 24, the central section 54 is coaxially disposed around the flexible intermediate portion 34 of the first tubular member 24. In one embodiment, a length $L_2$ of the central section 54 is slightly less than a length $L_1$ of the intermediate portion 34. When coaxially disposed, the flexible spiral cut central section 54 terminates along the flexible intermediate portion 54 between the first and second ends 36a, 36b. The proximal section 50 is coaxially disposed around and fixed to the proximal portion 30 and the distal section 52 is coaxially disposed around and fixed to the distal portion 32. The second tubular member 26 can be formed of a rigid material such as stainless steel, for example. The terminal ends of the proximal and distal sections 50, 52 can be fixedly secured to the proximal and distal portions 30, 32, respectively, by laser welding or other suitable means of bonding.

In some embodiments, the third tubular member 28 is included and coaxially disposed over the first and second tubular members 24, 26. The third tubular member 28 is similar to the second tubular member 26 and includes opposing proximal and distal sections 60, 62 and a central section 64 extending between the proximal and distal sections 60, 62. In one embodiment, the central section 64 includes a spiral cut pattern to provide longitudinal flexibility along the central section 64. The spiral cuts extend through a thickness of the third tubular member 28 between an outer and an inner surface. The spiral cut defines an angle with the central longitudinal axis of the third tubular member 28 in a generally opposite direction from the angle of the spiral cut of the central section 54 of the second tubular member 26. For example, when a left hand laser cut is provided on the second tubular member 26 a right hand laser cut is provided on the third tubular member 28. The spiral cut defines a flexible region along the length of the third tubular member 28. When assembled with the first and second tubular members 24, 26, the central section 64 is coaxially disposed along the flexible intermediate portion 34 and the central section 54. The central section 54 provides flexibility and torque transmittance along the flexible region of the first tubular member 24 as the inner member 20 is rotated within, and conforms to, the shape of the bent or angled outer member 18.

In one embodiment, the central section 64 has a length $L_3$ that is less than the length $L_2$ of the central section 54 and less than the length $L_1$ of the intermediate portion. Regardless, an overall length of the second tubular member 26 is greater than an overall length of the third tubular member 28 such that, when coaxially disposed, the proximal section 60 is fixed to the proximal section 50 and the distal section 62 is fixed to the distal section 52. In one embodiment, the third tubular member 28 is formed of a rigid material such as stainless steel, for example. The terminal ends of the proximal and distal sections 60, 62 can be fixedly secured to the proximal and distal sections 50, 52, respectively, by laser welding or other suitable means of bonding.

In another embodiment, the third tubular member 28 is formed of a flexible plastic material. For example, the third tubular member 28 can be formed of a thermoplastic material such as polytetrafluoroethylene (PTFE) or fluorinated ethylene propylene (FEP). The interior and exterior surfaces of the third tubular member 28 in this embodiment are generally smooth and are uninterrupted by grooves, cuts, etc. In this embodiment, the third tubular member 28 reduces the coefficient of friction between the inner tubular member 20 and the outer tubular member 18 as the inner tubular member 20 rotates within the outer tubular member 18. When assembled, the third tubular member 28 extends fully along the length of the central section 54 and terminates at the opposing proximal and distal sections 50, 52 of the second tubular member 26. The third tubular member 28 is fixedly secured to the second tubular member 26 via induction bonding or other suitable means.

The inner member 20 without the third tubular member 28 is suitable for surgical instruments that rotate in a single direction. The third tubular member 28 can be desirably included, for example, in an oscillating surgical instrument. In the embodiment including the third tubular member 28 having a spiral cut central section 64, by including spiral cuts in opposing directions on the second and third tubular members 26, 28, undesirable unwinding of the central section 54 when rotated in a direction opposite of the spiral cut of the second tubular member 26 during oscillation is prevented. In the embodiment including the third tubular member 28 formed of thermoplastic, undesirable unwinding of the central section 54 when rotated in a direction opposite of the spiral cut of the second tubular member 26 during oscillation is similarly prevented.

Although the present disclosure has been described with reference to preferred embodiments, workers skilled in the art will recognize that changes can be made in form and detail without departing from the spirit and scope of the present disclosure.

What is claimed is:

1. An inner member rotatable within an angled outer tubular member of a rotary surgical cutting instrument, comprising:
   a first tubular member, comprising:
      a rigid proximal portion comprised of a first material, the proximal portion extending between a joining end and a hub end including a hub;
      a flexible intermediate portion comprised of a second material, the second material different than the first material, the intermediate portion extending between opposing first and second ends; and
      a rigid distal portion comprised of the first material, the distal portion terminating at a distal end configured to couple with a cutting tip, and the distal portion terminating at a joining end opposite the distal end,
      wherein the flexible intermediate portion extends between the proximal portion and the distal portion, wherein the first end of the intermediate portion is fixedly coupled to the joining end of the proximal portion and the second end of the intermediate portion is fixedly coupled to the joining end of the distal portion; and
   a second tubular member coaxially disposed around the first tubular member along at least the intermediate portion, wherein the second tubular member is spiral cut in a first direction along a central section,
   wherein a first end of the second tubular member is fixedly attached to the proximal portion of the first tubular member and a second end of the second tubular member is fixedly attached to the distal portion of the first tubular member, and wherein the central section disposed around the intermediate portion defines a flexible region allowing the inner member to bend while being rotated within the outer tubular member.

2. The inner member of claim 1, further comprising:
a third tubular member coaxially disposed around the second tubular member, wherein the third tubular member is spiral cut in a second direction along a central section, and wherein the central section of the third tubular member is disposed over the central section of the second tubular member.

3. The inner member of claim 2, wherein the third tubular member extends fully along a length of the central section of the second tubular member and terminates at opposing rigid proximal and distal sections of the second tubular member.

4. The inner member of claim 2, wherein the second tubular member extends along the proximal and distal portions further than the third tubular member.

5. The inner member of claim 1, wherein the second material of the flexible intermediate portion is a thermoplastic material.

6. The inner member of claim 1, wherein the first material of the distal and proximal portions is stainless steel.

7. The inner member of claim 1, wherein the second tubular member is comprised of stainless steel.

8. The inner member of claim 1, wherein the second tubular member includes a distal section on a distal end of the central section and a proximal section on a proximal end of the central section, wherein the distal and proximal sections are not spiral cut.

9. An inner member rotatable within an angled outer tubular member of a rotary surgical instrument, comprising:
a first tubular member having a proximal portion, a distal portion, and an intermediate portion extending between the proximal portion and the distal portion, the intermediate portion including a first end fixedly coupled to a joining end of the proximal portion and a second end fixedly coupled to a joining end of the distal portion, wherein the proximal and distal portions are comprised of a rigid material, and wherein the intermediate portion is comprised of a flexible thermoplastic material; and
a second tubular member coaxially disposed around the first tubular member along the intermediate portion, the second tubular member having a proximal section, a distal section, and a central section extending between the proximal section and the distal section, wherein the central section is flexible and the proximal and distal sections are rigid,
wherein the proximal section is attached to the proximal portion and the distal section is attached to the distal portion, and
wherein the central section disposed over the intermediate portion define a flexible region of the inner member conforming to an angled region of an outer tubular member.

10. The inner member of claim 9, further comprising:
a third tubular member coaxially disposed around the second tubular member, the third tubular member having a proximal section, a distal section, and a central section extending between the proximal section and the distal section, wherein the central section is flexible and the proximal and distal sections are rigid.

11. The inner member of claim 9, further comprising:
a third tubular member coaxially disposed around the second tubular member, the third tubular member comprised of a thermoplastic material.

12. The inner member of claim 10, wherein the second tubular member has a length greater than a length of the third tubular member.

13. The inner member of claim 10, wherein the central section of the second tubular members is spiral cut at a first angle offset from a longitudinal axis and the central section of the third tubular member is spiral cut at a second angle different than the first angle.

14. The inner member of claim 9, wherein opposing ends of the second tubular member are bonded to the proximal and distal portions of the first tubular member.

15. The inner member of claim 9, wherein the central section is spiral cut.

16. An angled rotary tissue cutting instrument, comprising:
a rigid outer tubular member having a cutting window formed at a distal end, an opposing proximal end, and an angled region between the distal and proximal ends;
an inner tubular member coaxially disposed within the outer tubular member, the inner tubular member comprising:
a first tubular member having a proximal portion terminating at a first joining end, a distal portion terminating at a second joining end and a cutting tip opposite the second joining end, and an intermediate portion extending between the proximal portion and the distal portion, wherein a first end of the intermediate portion is fixedly coupled to the first joining end of the proximal portion and a second end of the intermediate portion is fixedly coupled to the second joining end of the distal portion, wherein the intermediate portion is comprised of a flexible material and the proximal and distal portions are comprised of a rigid material, the flexible material different than the rigid material; and
a handpiece configured to rotate the inner member within the outer member to selectively expose the cutting tip at the cutting window; and
a second tubular member coaxially disposed around the first tubular member along the intermediate portion, the second tubular member having a proximal section, a distal section, and a central section extending between the proximal section and the distal section, wherein the central section is flexible and the proximal and distal sections are rigid,
wherein the central section is disposed around the intermediate portion to define a flexible region of the inner tubular member,
wherein the proximal section is attached to the proximal portion and the distal section is attached to the distal portion,
wherein the intermediate portion of the inner tubular member conforms to the angled region while being rotated within the outer tubular member.

17. The surgical cutting instrument of claim 16, wherein the handpiece oscillates the inner tubular member, wherein the inner tubular member further comprises:
a third tubular member coaxially disposed around the second tubular member,
wherein the third tubular member extends along the central section of the second tubular member and terminates at the opposing distal and proximal sections of the second tubular member, and
wherein the third tubular member is at least partially flexible.

* * * * *